United States Patent [19]
Bruce et al.

[11] Patent Number: 5,299,559
[45] Date of Patent: Apr. 5, 1994

[54] ENDOSCOPE WITH OVERLOAD PROTECTIVE DEVICE

[75] Inventors: Douglas M. Bruce, Santa Cruz; Thomas G. Cooper, Menlo Park, both of Calif.; James E. Phetteplace, Westfield; Joseph F. Rosewarne, Turners Falls, both of Mass.

[73] Assignee: Acuson Corporation, Mountain View, Calif.

[21] Appl. No.: 850,933

[22] Filed: Mar. 13, 1992

[51] Int. Cl.$^5$ .............................................. A61B 1/00
[52] U.S. Cl. .......................................... 128/4; 604/95
[58] Field of Search ............................. 128/4, 6, 7, 8; 138/120; 604/95

[56] References Cited

U.S. PATENT DOCUMENTS

| | | | |
|---|---|---|---|
| 4,203,430 | 5/1980 | Takahashi | 128/4 |
| 4,294,233 | 10/1981 | Takahashi | 128/4 |
| 4,483,326 | 11/1984 | Yamaka et al. | 128/4 |
| 4,718,407 | 1/1988 | Chikama | 128/4 |
| 4,787,369 | 11/1988 | Allred, III et al. | 128/4 |
| 5,025,804 | 6/1991 | Kondo | 128/4 |

FOREIGN PATENT DOCUMENTS 3421930  12/1984  Fed. Rep. of Germany .......... 128/4

*Primary Examiner*—Richard J. Apley
*Assistant Examiner*—Karen A. Jalbert
*Attorney, Agent, or Firm*—Ernest M. Anderson

[57] ABSTRACT

This invention provides an improved endoscope having control wires for articulating a set of rings and directing a probe which further provides an overload protection device interconnecting the control wires to an operating member. The overload protection device provides a controlled resiliency to inhibit the application of excess tension to the control wires but provides sufficient force to manipulate the probe.

6 Claims, 1 Drawing Sheet

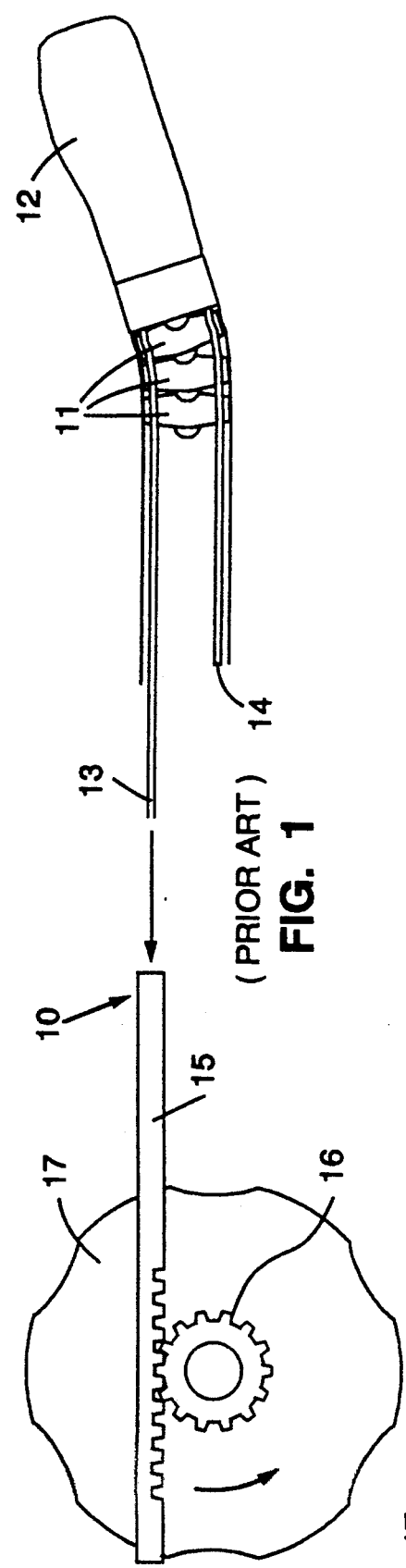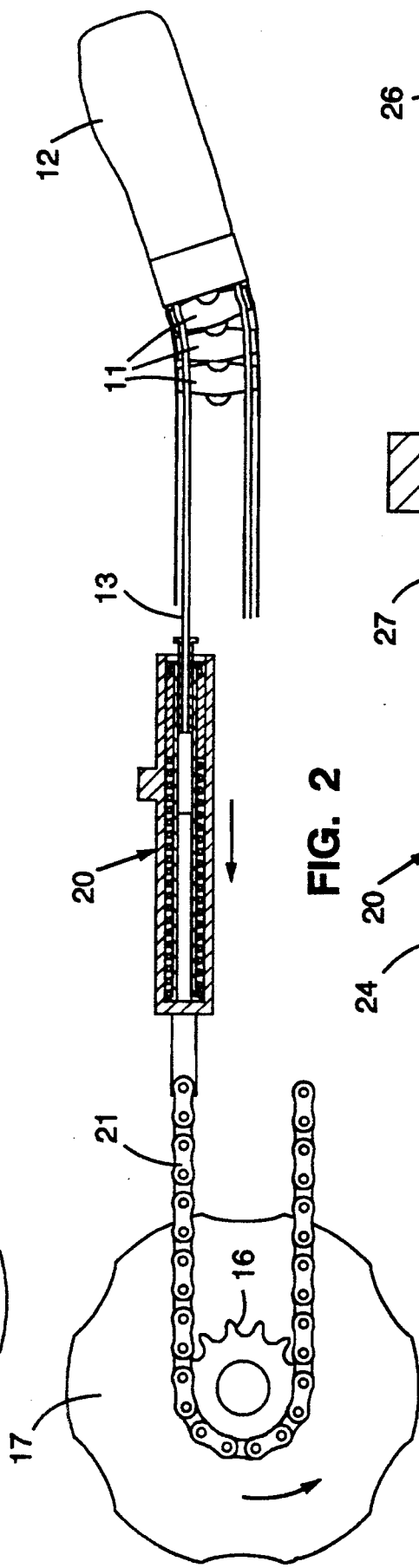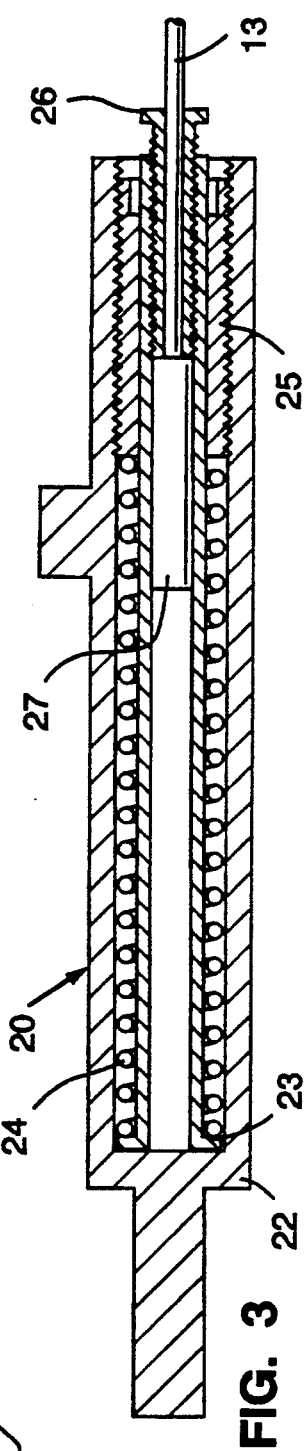

1

ENDOSCOPE WITH OVERLOAD PROTECTIVE DEVICE

BACKGROUND OF THE INVENTION

This invention relates generally to endoscopes and more particularly to a means for limiting the amount of tension applied to control wires which are utilized to direct or redirect a probe. Endoscopes are currently known which utilize a set of articulated rings with means for bending or articulating the rings to direct the probe. For that purpose, a pair of control wires is employed to articulate the rings, and motion is produced by applying tension to one of the control wires. Wire tension is typically generated by rotation of a control knob, the motion of which is translated through a mechanism, such as a rack and pinion, to pull on one wire while simultaneously releasing tension or producing slack in a second control wire which rotates the rings in the opposite direction.

SUMMARY OF THE INVENTION

This invention relates to an overload protective device for endoscopes to improve operation and endurance and to avoid over-tensioning of the control wires or fatigue failures caused by repeat overloads. The device also operates to limit the forces applied and, thus, acts as a safety feature to prevent tissue damage. The invention more particularly provides a spring mechanism that interconnects each of the control wires with the operating member including means for limiting the tension applied to the wires to preset values. It also includes means for adjustably setting the slack or tension maintained in the wires.

Various objects of the invention will become apparent in view of the following detailed description.

BRIEF DESCRIPTION OF THE DRAWINGS

FIG. 1 is a diagrammatic view of a conventional mechanism for operating the wires of an endoscope which is part of the prior art;

FIG. 2 is a preferred embodiment of the invention in an endoscope that includes a device for preventing overloads upon the control wires; and FIG. 3 is an enlarged detail view of the linkage means used in connection with the embodiment of FIG. 2.

Referring to FIG. 1, there is shown a typical embodiment of a prior art endoscope 10 comprising a set of articulated rings 11 having a probe 12 mounted to one end thereof. Rings 11 are interconnected and articulated one to the other by a pair of control wires 13 and 14. Each wire extends through an opening of each ring, but on opposite sides, and each is connected to the endmost link adjacent to the probe. Applying tension to wire 13, as indicated, rotates the links relative to each other as shown, thereby directing probe 12. A rack bar 15 engaged with a pinion 16 is moved linearly as the pinion is rotated by an operating knob 17. Rotation of the knob imparts the necessary tensioning force for rotating links 11 and turning probe 12. A similar interconnection of parts (not shown) is utilized to apply tension to control wire 14 and rotate the probe in the opposite direction.

FIGS. 2 and 3 illustrate an improved apparatus for articulating the rings 11 to direct probe 12. In that regard an overload protection means 20 is provided to interconnect the control wire 13 with the operating member or knob 17. Means 20 provides a controlled resiliency to inhibit the application of excess tension and limits the tension applied to the wire to preset values. Means is also provided for adjustably setting the slack or tension maintained in the wires. In the preferred embodiment shown, the invention includes a chain 21 that engages the gear 16. The use of a chain and gear in lieu of a rack and pinion is particularly useful in conjunction with the overload protection means, reducing wear and improving reliability.

FIG. 3 illustrates the construction of the overload protection means 20 more clearly, which comprises a cylinder 22 that connects to pinion 16 and operating member 17 through chain 21. A piston member 23 is slidably received within cylinder 22, and a helical spring 24 engages with the piston, resiliently biasing the piston into the cylinder to the extent that the end of the piston is seated against the inner end wall of the cylinder. A spring retainer 25 captures the spring 24 within the cylinder and between the cylinder and the longitudinal stem or wall of the piston. Spring retainer 25 has external threads which threadably engage the internal threads provided in the end of cylinder 22. Accordingly, the axial position of spring retainer 25 is adjusted within cylinder 22 to adjust the force or bias imposed upon piston 23 by spring 24. Thus, threadably adjusting the position of spring retainer 25 relative to cylinder 22 presets the biasing force.

Means is further provided connecting piston 23 to control wire 13 for setting the slack or operating tension in the wire. A sleeve 26 is provided with exterior threads that engage with internal threads provided in the stem end of piston 23. Wire 13 extends through the bore of sleeve 26 and is secured to a holdback member 27 of greater size than the bore of sleeve 26. Therefore, threaded adjustments of sleeve 26 move or reposition the holdback member within the bore of piston 24. This permits an adjustment in slack or tension to be maintained in the wire independently of the spring tension and overload setting of spring 24.

Although a preferred embodiment of the invention has been illustrated and described, various modifications and changes may be resorted to without departing from the spirit of the invention or the scope of the appended claims, and each of such modifications and changes is contemplated.

What is claimed is:

1. An endoscope comprising a set of articulated rings, a probe mounted to one end of said rings, means for articulating said rings to direct or redirect said probe including a rotatable operating member and a wire connected to said articulated rings; wherein an overload protection means interconnects said wire to said operating member, said overload protection means providing controlled resiliency to inhibit the application of excess tension to said wire and comprising a cylinder connected to said operating member, a piston connected to said wire and slidably received within said cylinder, a spring engaged with said piston and resiliently biasing said piston into said cylinder, and a spring retainer for capturing said spring within said cylinder and applying a preset biasing force upon said piston.

2. The endoscope of claim 1, said overload protection means further including an adjustable means intermediate said piston and wire for setting the slack or operating tension in said wire.

3. The endoscope of claim 2, said piston being internally threaded, said adjustable means intermediate said piston and wire comprising an externally threaded sleeve threadably engaged with said piston, and means connecting said wire to said sleeve for setting the slack or tension in said wire upon threaded adjustments between said piston and sleeve.

4. An overload protection device for use in an endoscope having a probe and means for articulating the probe, including a pair of wires connected to a rotatable operating member, and means for interconnecting a wire to the operating member to provide controlled resiliency that inhibits the application of excess tension in said wire, said overload protection device comprising:

a cylinder adapted for connection to the operating member, a piston adapted for connection to the wire and slidably received within said cylinder, a spring engaged with said piston and resiliently biasing said piston into said cylinder, and a spring retainer capturing said spring within said cylinder and applying a preset biasing force to said piston.

5. The overload protection device of claim 4, and further including an adjustable means intermediate said piston and wire for setting the slack or operating tension applied to the wire.

6. The overload protection device of claim 5, said piston being internally threaded, said adjustable means intermediate said piston and wire comprising an externally threaded sleeve threadably engaged with said piston, and means for connecting the wire to said sleeve to set the slack or tension in the wire upon threaded adjustments between said piston and sleeve.

* * * * *